US012571003B2

(12) United States Patent
Chang et al.

(10) Patent No.: US 12,571,003 B2
(45) Date of Patent: \*Mar. 10, 2026

(54) ELECTROPORATION WITH ACTIVE COMPENSATION

(71) Applicant: NantCell, Inc., Culver City, CA (US)

(72) Inventors: Chih-wei Chang, Los Angeles, CA (US); Jon Thomas Van Lew, Los Angeles, CA (US); Artin Mehrabi, Burbank, CA (US)

(73) Assignee: NantCell, Inc., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/616,672

(22) Filed: Mar. 26, 2024

(65) Prior Publication Data

US 2024/0229074 A1 Jul. 11, 2024

Related U.S. Application Data

(63) Continuation of application No. 16/935,987, filed on Jul. 22, 2020, now Pat. No. 12,006,507.

(51) Int. Cl.
*C12N 15/00* (2006.01)
*A61N 1/00* (2006.01)
(Continued)

(52) U.S. Cl.
CPC .............. *C12N 15/87* (2013.01); *A61N 1/08* (2013.01); *C12M 35/02* (2013.01); *A61N 1/0476* (2013.01); *A61N 1/378* (2013.01); *H03K 3/00* (2013.01)

(58) Field of Classification Search
CPC .............................. C12M 35/02; A61N 1/0476
See application file for complete search history.

(56) References Cited

U.S. PATENT DOCUMENTS 5,676,646 A 10/1997 Hofmann et al.
6,387,671 B1 5/2002 Rubinsky et al.
(Continued)

FOREIGN PATENT DOCUMENTS

CN 101857836 A 10/2010
WO 2006112870 A1 10/2006
(Continued)

OTHER PUBLICATIONS

Non-Final Office Action from U.S. Appl. No. 16/935,987 dated Jan. 8, 2024.

*Primary Examiner* — Nathan A Bowers
(74) *Attorney, Agent, or Firm* — Harness Dickey & Pierce P.L.C.

(57) ABSTRACT

An apparatus for electroporating cells with a cargo includes electrodes defining a path for a fluid including the cells and the cargo to flow, a power source coupled across the electrodes, and a control circuit. In some examples, the control circuit is configured to detect a decrease in an induced current due to an increase in a resistance between the electrodes, and control the power source to increase the induced current to maintain an electric field between the electrodes. A future value of the resistance between the electrodes may be predicted based on previous values of the resistance. In other examples, the control circuit is configured to detect parameters of the fluid flowing between the electrodes, and control the power source to generate or stop generating electrical pulses in response to detecting the parameters. Other example apparatuses, and methods of electroporating cells with a cargo is also disclosed.

5 Claims, 14 Drawing Sheets

(51) Int. Cl.

| | |
|---|---|
| *A61N 1/08* | (2006.01) |
| *C12M 1/42* | (2006.01) |
| *C12N 15/87* | (2006.01) |
| *A61N 1/04* | (2006.01) |
| *A61N 1/378* | (2006.01) |
| *H03K 3/00* | (2006.01) |

(56) References Cited

U.S. PATENT DOCUMENTS

| | | | |
|---|---|---|---|
| 6,403,348 B1 | 6/2002 | Rubinsky et al. | |
| 6,482,619 B1 | 11/2002 | Rubinsky et al. | |
| 6,801,804 B2 | 10/2004 | Miller et al. | |
| 7,029,916 B2 | 4/2006 | Dzekunov et al. | |
| 7,141,425 B2 | 11/2006 | Dzekunov et al. | |
| 7,245,963 B2 | 7/2007 | Draghia-Akli et al. | |
| 8,222,909 B2 | 7/2012 | Ragsdale | |
| 9,452,285 B2 | 9/2016 | Draghia-Akli et al. | |
| 10,252,269 B2 | 4/2019 | Kung et al. | |
| 2017/0067007 A1 | 3/2017 | Miltenyi et al. | |
| 2017/0283761 A1 | 10/2017 | Corso | |
| 2017/0291172 A1 | 10/2017 | Kung et al. | |
| 2018/0258379 A1 | 9/2018 | Zahn et al. | |
| 2019/0100722 A1* | 4/2019 | Bernate ................. | C12N 15/70 |
| 2019/0117964 A1 | 4/2019 | Bahrami et al. | |
| 2020/0017847 A1 | 1/2020 | Chang | |
| 2022/0025402 A1 | 1/2022 | Chang et al. | |

FOREIGN PATENT DOCUMENTS

| | | | |
|---|---|---|---|
| WO | 2015027923 A1 | 3/2015 |
| WO | 2018075989 A1 | 4/2018 |

* cited by examiner

N-844-2 (α-CTLA4/TxM-B) Fusion Protein Production Titer

ELECTROPORATION WITH ACTIVE COMPENSATION

CROSS-REFERENCE TO RELATED APPLICATIONS

This application is a continuation of U.S. patent application Ser. No. 16/935,987 filed Jul. 22, 2020. The entire disclosure of the above application is incorporated herein by reference.

FIELD

The present disclosure relates to electroporation with active compensation.

BACKGROUND

This section provides background information related to the present disclosure which is not necessarily prior art.

Transfection is commonly used to introduce nucleic acids into cells to produce genetically modified cells. Various physical, chemical and viral methods exist for transfecting cells, including optoperforation, polymer based methods utilizing calcium phosphate, microinjection, electroporation, viral transduction, and lipid mediated methods (e.g., using liposome-DNA complexes). When electroporation is used to transfect a cell, controlled direct current (DC) electrical pulses are applied to the cell to induce a transmembrane potential. This transmembrane potential causes a reversible breakdown of the ordered structure of a cell membrane, leading to the formation of pores in the membrane. Molecules of interest can then enter the cell through the pores. Pore formation can be controlled by adjusting various parameters, including a distance between parallel electrodes used in the electroporation process, characteristics of the electrical pulses, an electric field strength across the electrodes, etc.

SUMMARY

This section provides a general summary of the disclosure, and is not a comprehensive disclosure of its full scope or all of its features.

According to one aspect of the present disclosure, an apparatus for electroporating cells with a cargo is presented. The apparatus includes two electrodes spaced apart from each other and defining a path for a fluid including the cells and the cargo to flow therebetween, a DC power source coupled across the electrodes, and a control circuit. The electrodes having a resistance therebetween when fluid flows through the path. The control circuit is configured to control the DC power source to provide a plurality of electrical pulses at a voltage to the electrodes to induce a current through the electrodes for generating an electric field between the electrodes at a defined value, detect a decrease in the induced current due to an increase in the resistance between the electrodes, and control the DC power source to increase the induced current to maintain the electric field between the electrodes at the defined value.

According to another aspect of the present disclosure, an apparatus for electroporating cells with a cargo is presented. The apparatus includes two electrodes spaced apart from each other and defining a path for a fluid including the cells and the cargo to flow therebetween, a DC power source coupled across the electrodes for providing a plurality of electrical pulses to induce a current through the electrodes for generating an electric field between the electrodes, and a control circuit configured to detect a first parameter associated with the fluid, in response to detecting the first parameter associated with the fluid, control the DC power source to generate the plurality of electrical pulses, detect a second parameter associated with the fluid, and in response to detecting the second parameter associated with the fluid, control the DC power source to stop generating the plurality of electrical pulses.

According to another aspect of the present disclosure, an apparatus for electroporating cells with a cargo is presented. The apparatus includes two electrodes spaced apart from each other and defining a path for a fluid including the cells and the cargo to flow therebetween, a DC power source coupled across the electrodes, and a control circuit. The electrodes having a resistance therebetween when fluid flows through the path. The control circuit is configured to control the DC power source to provide a plurality of electrical pulses at a voltage to the electrodes to induce a current through the electrodes for generating an electric field between the electrodes at a defined value, detect a decrease in the induced current due to an increase in the resistance between the electrodes, determine a plurality of values of the resistance between the electrodes over a period of time, predict a future value of the resistance between the electrodes based on the determined plurality of values of the resistance, and control the DC power source to increase the induced current based on the future value of the resistance to maintain the electric field between the electrodes at the defined value.

According to another aspect of the present disclosure, a method of electroporating cells with a cargo is presented. The method includes flowing a fluid including the cells and the cargo in a path defined by two electrodes spaced apart from each other. The electrodes having a resistance therebetween when fluid flows through the path. The method further includes controlling a DC power source to provide a plurality of electrical pulses at a voltage to the electrodes to induce a current through the electrodes to generate an electric field between the electrodes at a defined value, detecting a decrease in the induced current due to an increase in the resistance between the electrodes, and controlling the DC power source to increase the induced current to maintain the electric field between the electrodes at the defined value.

According to another aspect of the present disclosure, a method of electroporating cells with a cargo is presented. The method includes flowing a fluid including the cells and the cargo in a path defined by two electrodes spaced apart from each other, detecting a first parameter associated with the fluid, in response to detecting the first parameter associated with the fluid, controlling a DC power source to generate a plurality of electrical pulses to induce a current through the electrodes for generating an electric field between the electrodes, detecting a second parameter associated with the fluid, and in response to detecting the second parameter associated with the fluid, controlling the DC power source to stop generating the plurality of electrical pulses.

According to another aspect of the present disclosure, a method of electroporating cells with a cargo is presented. The method includes flowing a fluid including the cells and the cargo in a path defined by two electrodes spaced apart from each other. The electrodes having a resistance therebetween when fluid flows through the path. The method further includes controlling a DC power source to provide a plurality of electrical pulses at a voltage to the electrodes to induce a current through the electrodes to generate an electric field between the electrodes at a defined value, detecting a decrease in the induced current due to an increase in the resistance between the electrodes, determining a plurality of values of the resistance between the electrodes over a period of time, predicting a future value of the resistance between the electrodes based on the determined plurality of values of the resistance, and controlling the DC power source to increase the induced current based on the future value of the resistance to maintain the electric field between the electrodes at the defined value.

Further aspects and areas of applicability will become apparent from the description provided herein. It should be understood that various aspects of this disclosure may be implemented individually or in combination with one or more other aspects. It should also be understood that the description and specific examples herein are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding (but not necessarily identical) parts and/or features throughout the several views of the drawings.

DETAILED DESCRIPTION

Figure 1:
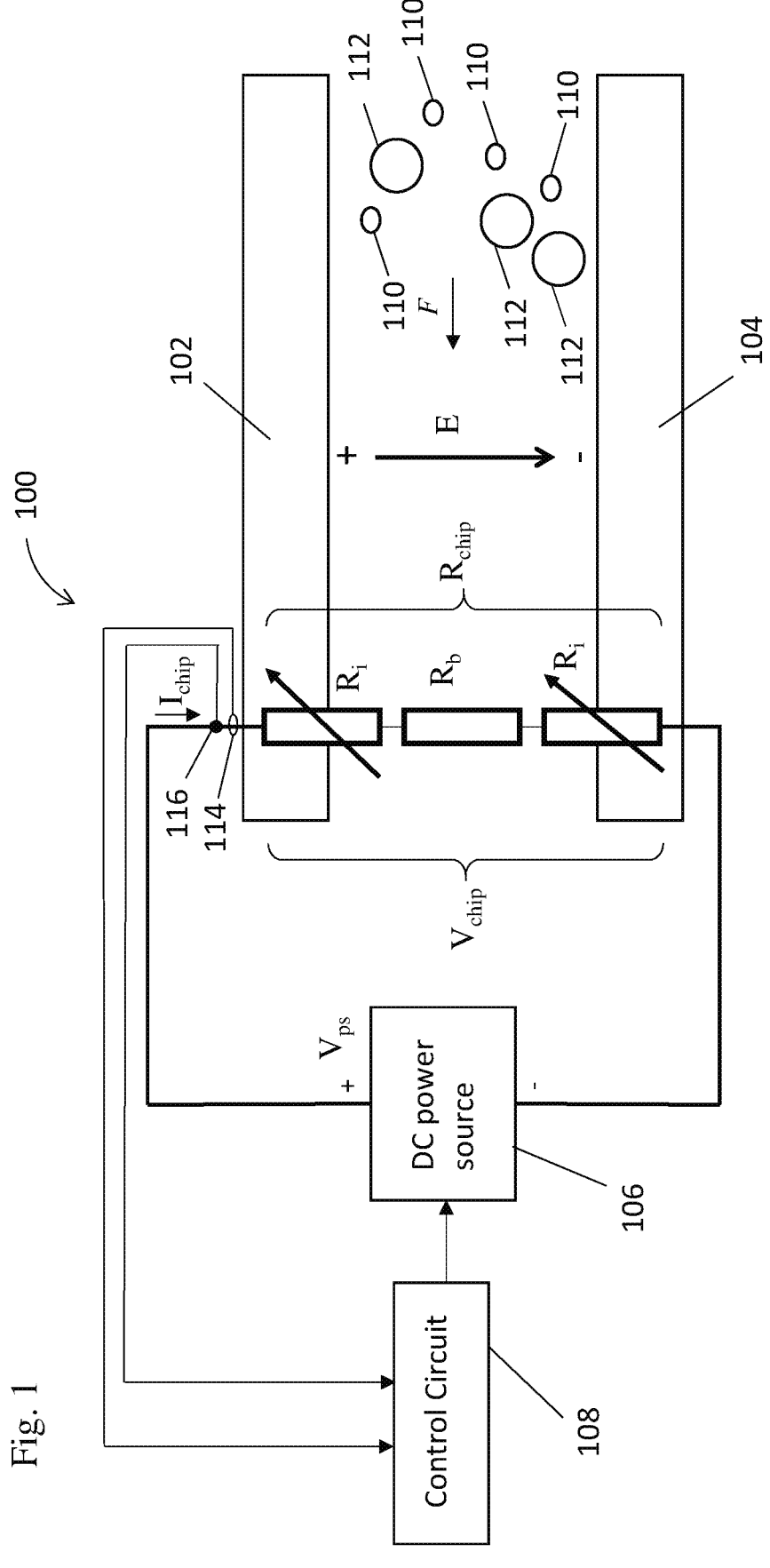
FIG. 1 is a block diagram of an electroporation apparatus employing active compensation to maintain an electric field strength according to one example embodiment of the present disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments will now be described more fully with reference to the accompanying drawings.

An apparatus for electroporating cells with a cargo according to one example embodiment of the present disclosure is illustrated in FIG. 1, and indicated generally by reference number 100. As shown in FIG. 1, the apparatus 100 includes two electrodes 102, 104, a DC power source 106 coupled across the electrodes, and a control circuit 108. The electrodes 102, 104 are spaced apart from each other and define a path for a fluid (shown generally with arrow F) including cells 112 and cargo 110 to flow therebetween. The electrodes have a resistance Rchip therebetween. The control circuit 108 controls the DC power source 106 to provide direct current (DC) electrical pulses at a voltage Vps to the electrodes 102, 104 to induce a current Ichip through the electrodes 102, 104 for generating an electric field E between the electrodes 102, 104, detects a decrease in the induced current Ichip due to an increase in the resistance Rchip between the electrodes, and controls the DC power source 106 to increase the induced current Ichip to maintain the electric field E between the electrodes 102, 104 at a defined value.

For example, the electrodes 102, 104 and associated components may form a chip. The electrodes 102, 104 and the fluid flowing between the electrodes 102, 104 may have the resistance Rchip (e.g., a resistance of the chip when fluid is present). In such examples, the resistance Rchip is equal to at least a resistance Rb of the fluid, and interface resistances Ri between the fluid and surfaces of the electrodes 102, 104. As shown in FIG. 1, the electric field E represents the effective electric field generated across the fluid (e.g., between the electrodes 102, 104) when the DC power source 106 provides the electrical pulses at the voltage Vps (e.g., a regulated voltage). In the particular example of FIG. 1, the electric field E is equal to a voltage Vchip (e.g., the voltage Vps less any voltage drop) across the electrodes 102, 104 divided by the distance between the electrodes 102, 104.

By increasing the induced current Ichip through the electrodes 102, 104, the transfection efficiency during electroporation may be maintained, and in some examples improved. For example, during electroporation, the resistance Rchip may increase over time as a function of the number of electrical pulses provided by the DC power source 106. In some examples, the increasing resistance Rchip may be caused by an increase in the interface resistance(s) Ri. In such examples, the increase in resistance may be due to, for example, charged molecules, DNA, protein, etc. attaching to surfaces of the electrodes 102, 104 causing electrode passivation, electrode degradation, etc. As a result of the increasing resistance Rchip, the induced current Ichip may fall and the effective electric field E across the fluid flowing between the electrodes 102, 104 may decrease. As a result, the transfection efficiency may reduce over time as further explained below. However, if the induced current Ichip flowing through the chip is increased, and in some examples maintained at a defined value, through active compensation (e.g., as further explained below), the effective electric field across the fluid and the transfection efficiency during electroporation may be maintained, and in some examples improved.

Figure 2:
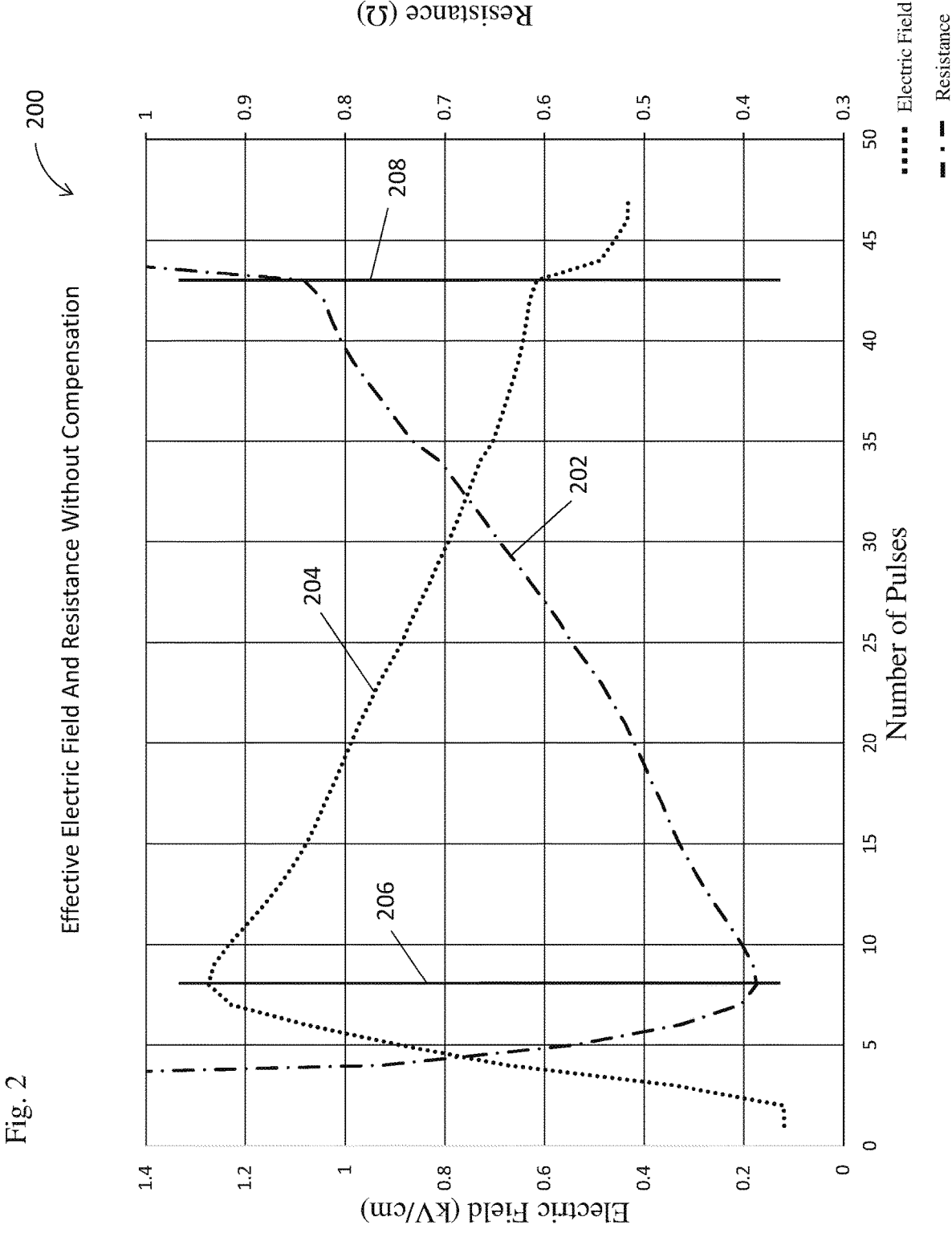
FIGS. 2-3 are graphs showing a voltage provided to electrodes of an electroporation apparatus, an induced current through the electrodes, and an increasing resistance between the electrodes causing degradation of an electric field strength when no active compensation is applied, according to another example embodiment.
Figure 3:
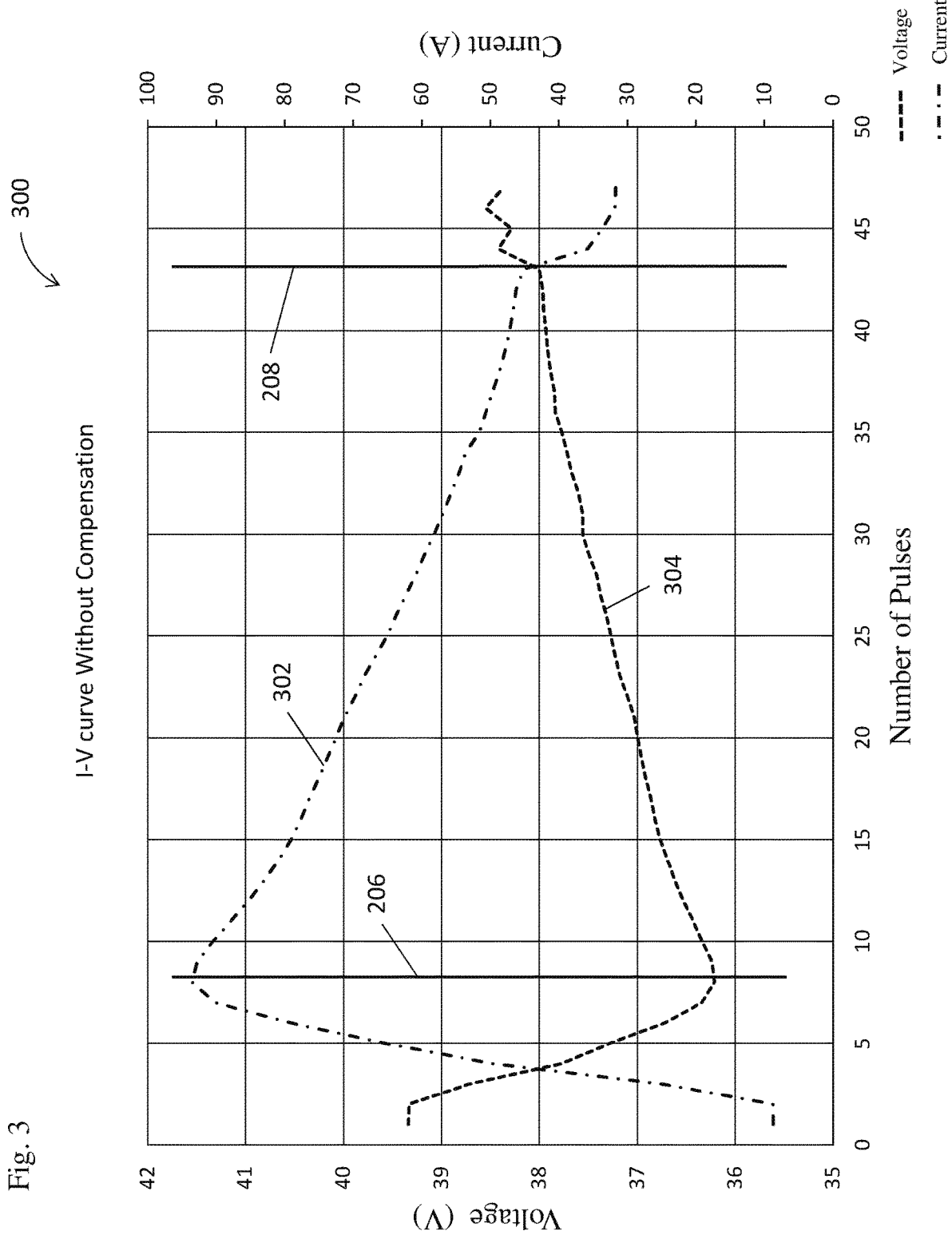

FIGS. 2 and 3 illustrates graphs 200, 300 showing electrical characteristics associated with the electrodes 102, 104 of FIG. 1 during electroporation when active compensation is not employed. In the particular example of FIGS. 2 and 3, the electrical characteristics relating to transfecting CHO-S cells with an expression plasmid containing the DNA encoding the α-CTLA-4/TxM-B fusion protein (e.g., the cargo) as described in Example 1 herein.

Specifically, FIG. 2 illustrates the resistance Rchip (line 202) associated with the chip, and the electric field E (line 204) across the fluid of FIG. 1. FIG. 3 illustrates the induced current Ichip (line 302) flowing through the chip, and the voltage Vchip (line 304) across the electrodes 102, 104. Testing has shown that the resistance Rchip (line 202) increases as the number of electrical pulses provided by the DC power source 106 increases. This increase in resistance begins when fluid enters the path (e.g., a chamber) between the electrodes 102, 104. In the particular example of FIG. 2, the resistance Rchip begins to increase around the seventh pulse, as shown by line 206 (e.g., when degradation begins). As the resistance increases over time, the induced current Ichip (line 302) flowing through the chip decreases and the voltage Vchip (line 304) increases as shown in FIGS. 2 and 3. During this time, the electric field E (line 204) begins to decrease at the line 206 and continues to degrade until the electroporation process ends at line 208.

Figure 4:
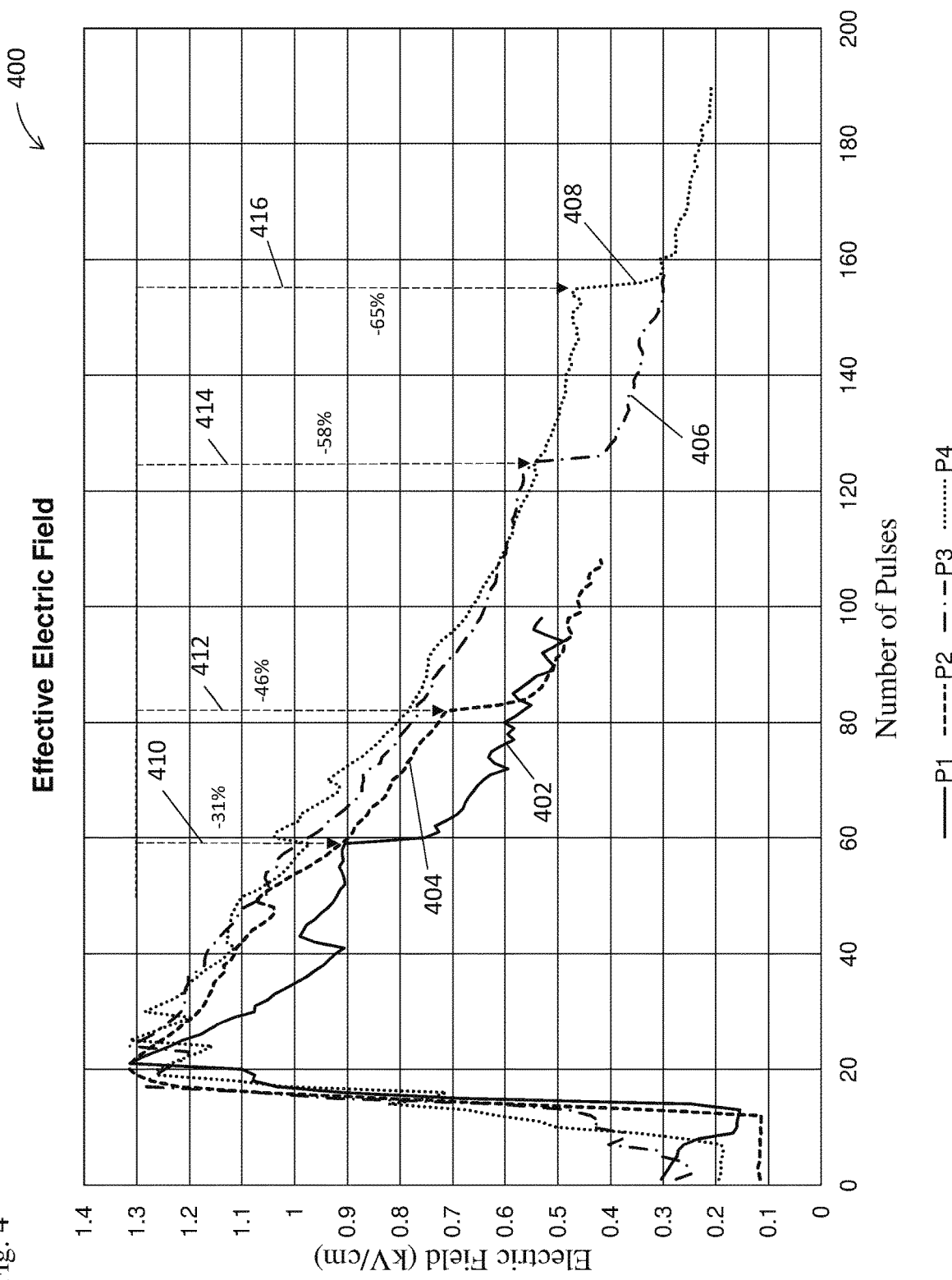
FIG. 4 is a graph showing degradation of electric field strengths for different electroporation processes with no active compensation according to another example embodiment.

FIG. 4 illustrates a graph 400 including lines 402, 404, 406, 408 representing electric fields for four experimental electroporation processes P1, P2, P3, P4 for transfecting CHO-S cells with an expression plasmid containing the DNA encoding the α-CTLA4/TxM-B fusion protein (e.g., the cargo) over different amounts of pulses, as described in Example 2 herein. Specifically, the line 402 (having a solid line configuration) represents the electric field during the electroporation process P1, the line 404 (having a dash-dash configuration) represents the electric field during the electroporation process P2, the line 406 (having a dash-dot-dash configuration) represents the electric field during the electroporation process P3, and the line 408 (having a dot-dot line configuration) represents the electric field during the electroporation process P4. See Example 2 herein.

As shown in FIG. 4 and Table 1 below, the effective electric field experiences a greater decrease as the volume of the fluid passing between the electrodes 102, 104 increases. The volume of the fluid is related to the number of electrical pulses received during each electroporation process P1, P2, P3, P4. For example, the electroporation process P1 processes 120 microliters (μL) of fluid (e.g., a duration of about 60 pulses) when the process P1 concludes at line 410, the electroporation process P2 processes 240 μL of fluid (e.g., a duration of about 83 pulses) when the process P2 concludes at line 412, the electroporation process P3 processes 400 μL of fluid (e.g., a duration of about 125 pulses) when the process P3 concludes at line 414, and the electroporation process P4 processes 600 μL of fluid (e.g., a duration of about 155 pulses) when the process P4 concludes at line 416.

TABLE 1

| α-CTLA4/TxM-B | P1 | P2 | P3 | P4 |
|---|---|---|---|---|
| Volume (μL) | 120 | 240 | 400 | 600 |
| $E_{eff}$ high (kV/cm) | 1.31 | 1.31 | 1.31 | 1.31 |
| $E_{eff}$ end (kV/cm) | 0.90 | 0.71 | 0.54 | 0.46 |
| $E_{eff}$ Percent Change | 31% | 46% | 58% | 65% |
| Titer (μg/mL) at Day 4 | 34.5 | 24.7 | 27.2 | 22.0 |

As shown in FIG. 4, the effective electric fields (lines 402, 404, 406, 408) associated with the electroporation processes P1, P2, P3, P4 begin to degrade at about 20-25 pulses. The value of each effective electric field at this time is about 1.31 kV/cm, as shown in Table 1 above. When the electroporation processes P1, P2, P3, P4 conclude, the electric field (i.e., the line 402) associated with the process P1 is 0.9 kV/cm, the electric field (i.e., the line 404) associated with the process P2 is 0.71 kV/cm, the electric field (i.e., the line 406) associated with the process P3 is 0.54 kV/cm, and the electric field (i.e., the line 408) associated with the process P4 is 0.46 kV/cm, as shown in FIG. 4 and Table 1 above. As such, the electric field experienced during the electroporation process P1 has a percent change of 31%, the electric field experienced during the electroporation process P2 has a percent change of 46%, the electric field experienced during the electroporation process P3 has a percent change of 58%, and the electric field experienced during the electroporation process P4 has a percent change of 65%, as shown in Table 1 above. Thus, as more fluid is passed between the electrodes 102, 104, the effective electric field experiences a greater decrease.

Additionally, yields associated with the electroporation processes P1, P2, P3, P4 may decrease as the volume of the fluid passing between the electrodes 102, 104 increases (e.g., the number of electrical pulses increase). For example, and as shown in Table 1 above, the titer for electroporation process P1 is 34.5 µg/mL at Day 4, the titer for electroporation process P2 is 24.7 µg/mL at Day 4, the titer for electroporation process P3 is 27.2 µg/mL at Day 4, and the titer for electroporation process P4 is 22 µg/mL at Day 4. As such, the concentration of CHO-S cells being transfected with the α-CTLA4/TxM-B protein decreases when the electric fields associated with the electroporation processes P1, P2, P3, P4 degrade, as shown in FIG. 4. Thus, the transfection efficiency may decrease as the electric field E decreases.

However, the transfection efficiency may be maintained at a desired level throughout the electroporation process by ensuring the effective electric field across the fluid is sufficient. For example, and with reference to FIG. 1, the control circuit 108 may monitor the induced current Ichip through the electrodes 102, 104 with a current sensor 114. In such examples, the control circuit 108 may monitor the current Ichip to detect a peak current value. When a decrease in the current Ichip is detected (e.g., when the current Ichip reaches a peak current value and falls) signifying degradation of the effective electric field E, the control circuit 108 controls the DC power source 106 to increase and maintain the current Ichip at a defined value such as the peak current value, a desired value below the peak current value, etc. Thus, in this particular example, the control circuit 108 controls the DC power source 106 to maintain the current Ichip at the defined value (e.g., starting the compensation process) in response to detecting the decrease in current provided by the DC power source 106.

In other examples, the control circuit 108 may monitor the voltage Vchip across the electrodes 102, 104 with a voltage sensor 116, and control the DC power source 106 to maintain the current Ichip at the defined value in response to the voltage Vchip being equal to or greater than a defined voltage threshold. For example, the voltage Vchip may begin to increase when degradation of the effective electric field E occurs, as explained above. In such examples, the control circuit 108 may detect when the voltage Vchip begins to increase by comparing the voltage to a defined voltage threshold. In response to the voltage Vchip reaching or exceeding the defined voltage threshold, the control circuit 108 may control the DC power source 106 to maintain the current Ichip at the defined value as explained herein.

The induced current Ichip may be maintained by actively compensating for the loss of current. For example, the current Ichip may be maintained by adjusting the voltage Vps provided by the DC power source 106 and/or the induced current Ichip. The voltage Vps and/or the current Ichip may be adjusted one time or multiple times (e.g., randomly or periodically based on sensed parameters, etc.) during the electroporation process. In some examples, the voltage Vps and/or the current Ichip may be adjusted to a fixed constant value. In other examples, the voltage Vps and/or the current Ichip may be adjusted according to a desired positive/negative slope, according to a mathematical expression (e.g., a polynomial function), etc. For example, the DC power source 106 may be controlled to provide a different (e.g., a higher) current to compensate for the decreasing current. In other examples, the DC power source 106 may be controlled to provide a different voltage to compensate for the decreasing current. In such examples, the voltage provided by the DC power source 106 may be changed. For example, the control circuit 108 may control the DC power source 106 to increase the voltage to a peak voltage value, regulate the voltage at a different set value, etc.

For example, given a chip voltage Vchip supplied to the chip, the induced current Ichip flowing through the chip of FIG. 1 is a function of the total chip resistance Rchip. In such examples, equation (1) below represents this relationship. As explained above, the resistance Rchip may increase as a function of the number of electrical pulses provided by the DC power source 106, as shown in equation (2) below. As a result of the increased resistance Rchip, the current Ichip decreases over time.

$$Vchip = Ichip \cdot Rchip \qquad \text{Equation (1)}$$

$$Rchip = R \ (\# \text{ of pulses}) \qquad \text{Equation (2)}$$

The DC power source 106 may be controlled based on defined parameters to compensate for the decreasing current Ichip. For example, when the control circuit 108 detects a decrease in the current Ichip, the control circuit 108 may control the DC power source 106 to maintain the current Ichip at a defined value such as a peak current Ipeak, as shown in equation (3) below. In such examples, if it is desired for the DC power source 106 to provide the current Ichip at its peak value, equation (3) can be modified into equation (4) below. When the current Ichip is maintained at its peak value (e.g., a constant), the voltage is required to increase as the resistance increases. In some examples, the control circuit 108 may control the DC power source 106 to increase the voltage of the electrical pulses to a peak voltage value Vpeak or another suitable value.

$$Vpeak = Ipeak \cdot R0 \qquad \text{Equation (3)}$$

$$Vpeak/R0 = Ipeak = V \ (\# \text{ of pulses})/R \ (\# \text{ of pulses}) \qquad \text{Equation (4)}$$

Thus, to maintain the current Ichip at its peak constant value, the regulated voltage Vps provided by the DC power source 106 may be increased to a set value Vset based on the resistance that changes as a function of the number of electrical pulses and the defined current level (e.g., the peak current value), as shown in equation (5) below.

$$Vset = Ipeak \cdot R \ (\# \text{ of pulses}) \qquad \text{Equation (5)}$$

Figure 5:
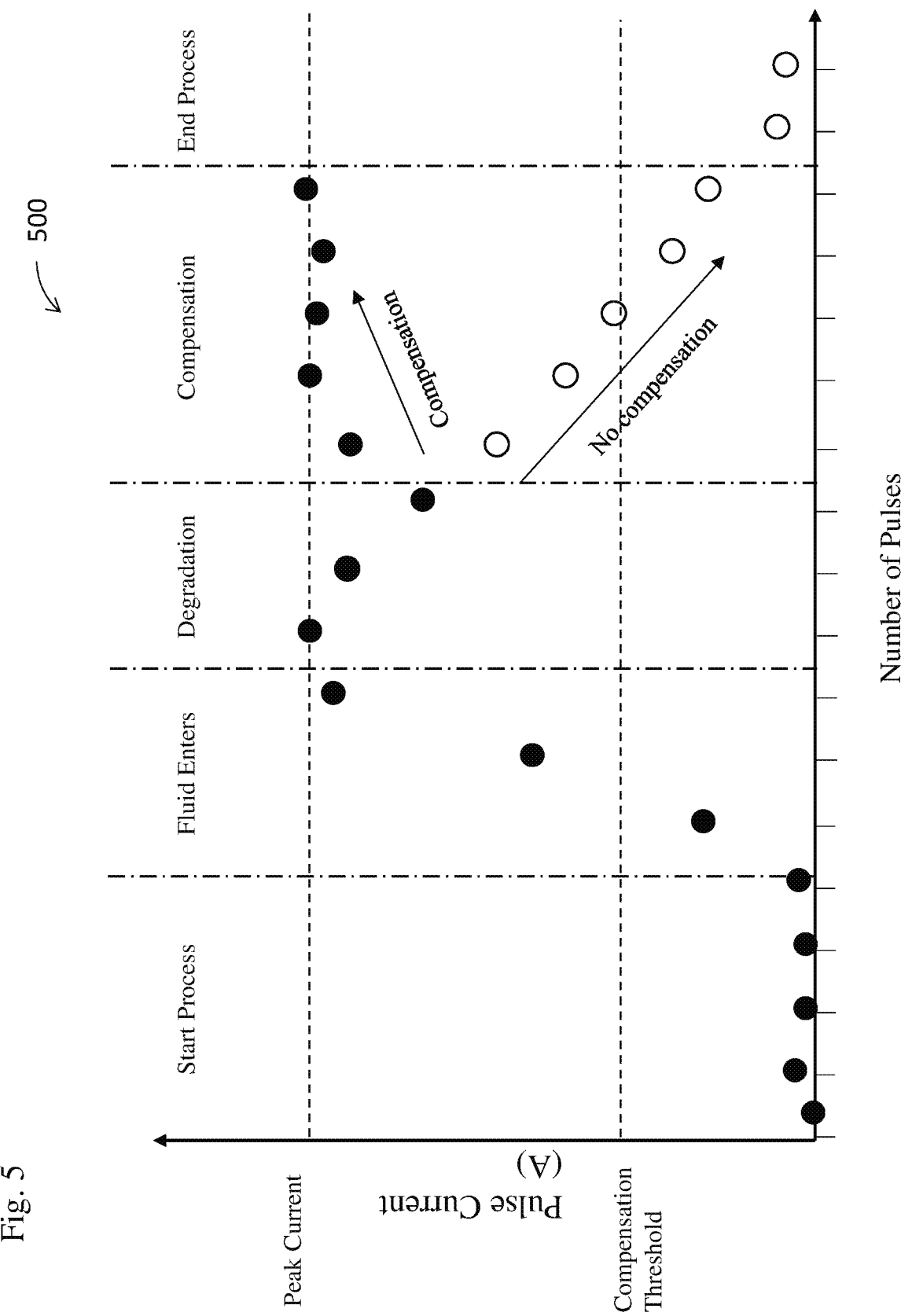
FIG. 5 is a graph showing an induced current through electrodes of an electroporation apparatus employing active compensation according to another example embodiment.

FIG. 5 illustrates a graph 500 showing the induced current Ichip of FIG. 1 changing over time. For example, the graph 500 is divided into five stages: (1) start of the electroporation process, (2) fluid flowing between the electrodes 102, 104, (3) degradation, (4) current compensation, and (5) completion of the electroporation process. As shown in FIG. 5, the current Ichip increases to a peak value when fluid flows between the electrodes 102, 104. When the control circuit 108 detects a decrease in the current Ichip (at the start of the degradation stage), the voltage Vps provided by the DC power source 106 is increased to the set value Vset. As a result, the current Ichip is increased to and maintained at the peak value (or another suitable defined value) during the compensation stage and until the electroporation process ends, as shown in FIG. 5. If the voltage Vps is not increased, the current Ichip decreases, as explained above.

The induced current Ichip may be required to exceed a threshold before compensation commences. For example, and as shown in FIG. 5, the induced current Ichip may be required to exceed a compensation threshold before the control circuit 108 controls to the DC power source 106 to increase the current chip as explained herein. This may prevent the control circuit 108 from prematurely beginning the compensation stage when the induced current Ichip peaks due to noise as fluid enters the chamber.

In some examples, the current Ichip may be increased and/or maintained at the defined value (e.g., the peak current value) based on a responsive compensation technique. In such examples, the control circuit 108 of FIG. 1 may determine the increase in the resistance Rchip and then control the DC power source 106 to increase and/or maintain the induced current Ichip based on the determined increase in the resistance between the electrodes 102, 104. This process of determining the change in resistance, and controlling the DC power source 106 based on the change in resistance may be repeated as desired. For example, when it is desired to maintain the current Ichip at its peak current value, the peak current value may be determined based on a system voltage Vsys and a system resistance Rsys (e.g., the resistance Rchip and any parasitic resistances), as shown in equation (6) below. In such examples, if the resistance Rsys increases due to degradation (as explained above), the voltage Vsys increases and the current Ichip remains constant at the peak current value. The resistance Rsys may be determined based on measured values of the voltage and current, as shown in equation (7) below.

$$Vsys = Ipeak \cdot Rsys \qquad \text{Equation (6)}$$

$$Rsys = Vmeas/Imeas \qquad \text{Equation (7)}$$

As explained above, the DC power source 106 is controlled to maintain the current Ichip at the peak current value. For example, the voltage Vsys may be changed to maintain the current Ichip. In such examples, the new system voltage Vsys, new may be determined based on the changing resistance as shown in equation (8) below, when using equations (6) and (7) above. The voltage Vsys may be changed multiple times (e.g., Vsys, new1, Vsys, new2, etc.) as the resistance Rsys continues to change over time.

$$Vsys, \text{new} = Ipeak \cdot (Vmeas/Imeas) \qquad \text{Equation (8)}$$

In some examples, the current Ichip may trend downward before the control circuit 108 begins the current compensation stage, as shown in FIG. 5. In such examples, a projected voltage and current may be used for the first compensation value (instead of the measured values of the voltage and current), as shown in equation (9) below.

$$Vsys, \text{new} = Ipeak \cdot (Vprojected/Iprojected) \qquad \text{Equation (9)}$$

Additionally, a feedback gain factor may be introduced to account for kinematics of the system. For example, the voltage difference $\Delta V$ between a value of the new voltage Vsys, new and a previous value of the voltage Vsys, previous may be determined with equation (10) below. In such examples, the DC power source 106 may be controlled to provide a set voltage Vsys, set based on the voltage difference $\Delta V$ and a feedback gain factor G as shown in equation (11) below. The feedback gain factor G may be a fixed value, or a variable value such as a machine learned value from previous compensation results (based on on-line computations, an off-line database, etc.), etc.

$$\Delta V = Vsys, \text{new} - Vsys, \text{previous} \qquad \text{Equation (10)}$$

$$Vsys, \text{set} = G \cdot \Delta V \qquad \text{Equation (11)}$$

In other examples, the induced current Ichip may be increased and/or maintained at the defined value (e.g., the peak current value) based on a predictive compensation technique. In such examples, the control circuit 108 of FIG. 1 may predict a future value of the resistance Rchip between the electrodes 102, 104, and then control the DC power source 106 to increase and/or maintain the current Ichip at the defined value (e.g., the peak current value) based on the predicted value of the resistance. For example, the control circuit 108 may determine the resistance Rchip (e.g., values of the changing resistance) between the electrodes 102, 104 multiple times, and apply a linear projection between the determined resistances to predict a future value of the resistance. The linear projection may be applied based on, for example, an 'all data' linear projection, or a 'moving window' linear projection, as further explained below.

Figure 6:
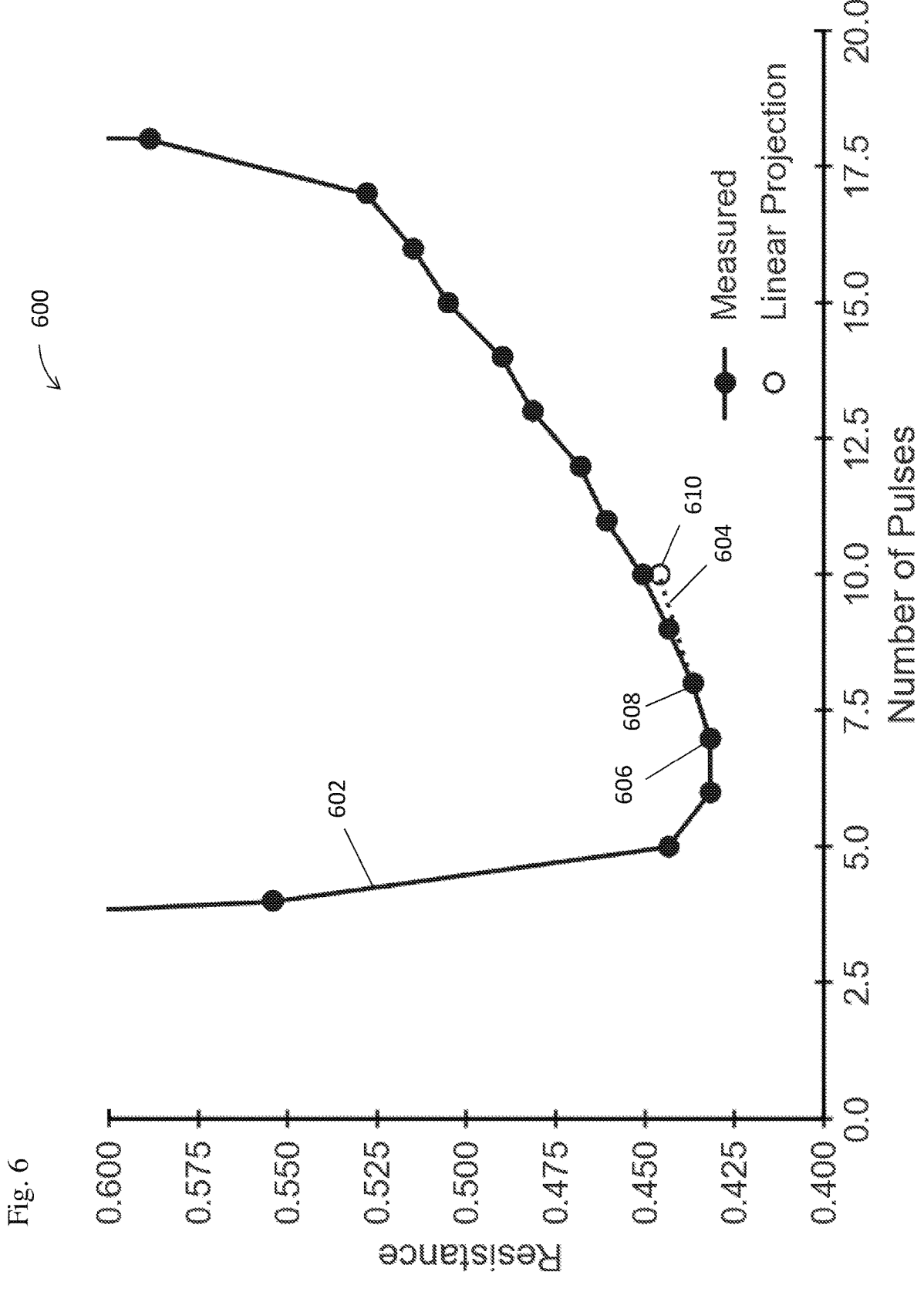
FIGS. 6-7 are graphs showing a predictive compensation technique employing an 'all data' linear projection according to another example embodiment.

For example, FIG. 6 illustrates a graph 600 including measured values of the chip resistance Rchip (line 602), and a linear projection (line 604) applied based on an 'all data' linear projection. In this example, the chip resistance Rchip is assumed to increase linearly as a function of the number of electrical pulses provided by the DC power source 106 throughout the entire degradation period. In this particular example, the control circuit 108 determines a peak current value after detecting a decreasing current at two consecutive pulses. At the peak current, the value of the chip resistance Rchip is determined (at point 606 of the line 602). For example, the value of the chip resistance Rchip at the peak current may be determined based on measurements of the current and the voltage, as explained above. This peak current value corresponds to a minimum value of the chip resistance Rchip before it begins to increase during degradation. At the peak current (and the minimum resistance), the pulse point value P is set to equal 0. After two consecutive pulses of decreasing current, the value of the chip resistance Rchip is determined again (at point 608 of the line 602). At this current, the pulse point value P is set to equal n.

Next, a linear projection (the dashed line 604) may be applied (e.g., linearly fit) from the pulse point value P=0 (the peak current) at the point 606 to the pulse point value P=n (the most recent pulse point) at the point 608. This linear projection may be used to predict a future value of the resistance (R_n+1) at the next pulse (e.g., the pulse point value P=n+1) due to electrode degradation. This is shown as point 610 on the linear projection line 604. After the resistance (R_n+1) is predicted, the power source 106 may be controlled to provide a new voltage Vsys, new based on the predicted resistance value and the defined value (e.g., the peak current value) of the current Ichip, as shown in equation (12) below.

$$Vsys, \text{new} = Ipeak \cdot R\_n + 1 \qquad \text{Equation (12)}$$

Figure 7:
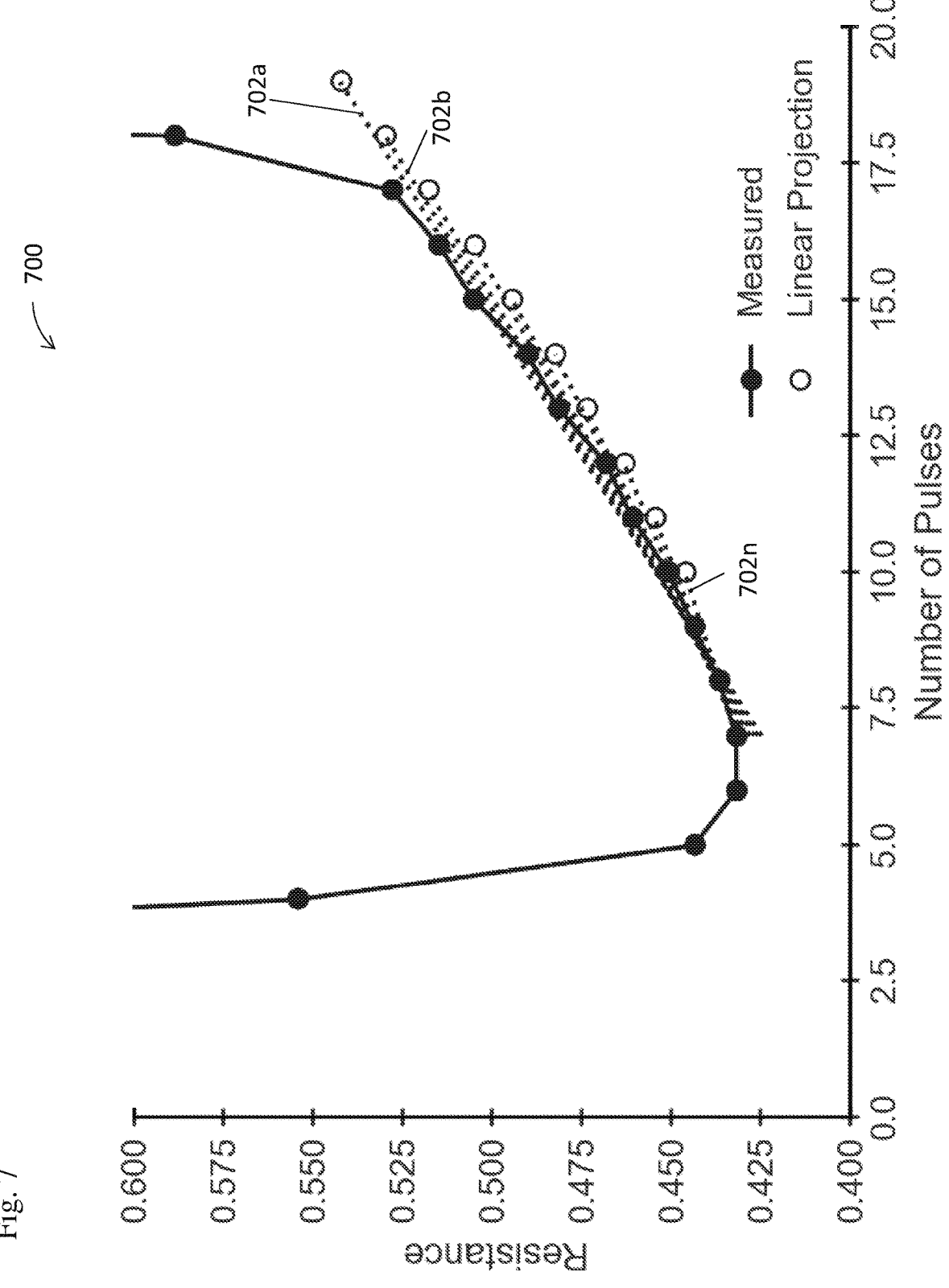

The 'all data' linear projection process may be repeated as desired (e.g., to the end of the electroporation process) to predict the resistance at the next pulse (R_n+2, R_n+3) and determine the voltage required to maintain the current Ichip at the defined value. For example, FIG. 7 illustrates a graph 700 showing multiple linear projections (e.g., dashed lines 702*a-n*) being applied to predict resistance values at future pulses. By using the 'all data' linear projection shown in FIGS. 6 and 7, the applied linear projections, and therefore the predicted values of the resistance, may be less prone to erratic voltage changes due to noise experienced when determining the resistance values. However, using the 'all data' linear projection method may not provide accurate predications if the chip resistance Rchip changes non-linearly (e.g., a non-linear degradation).

Figure 8:
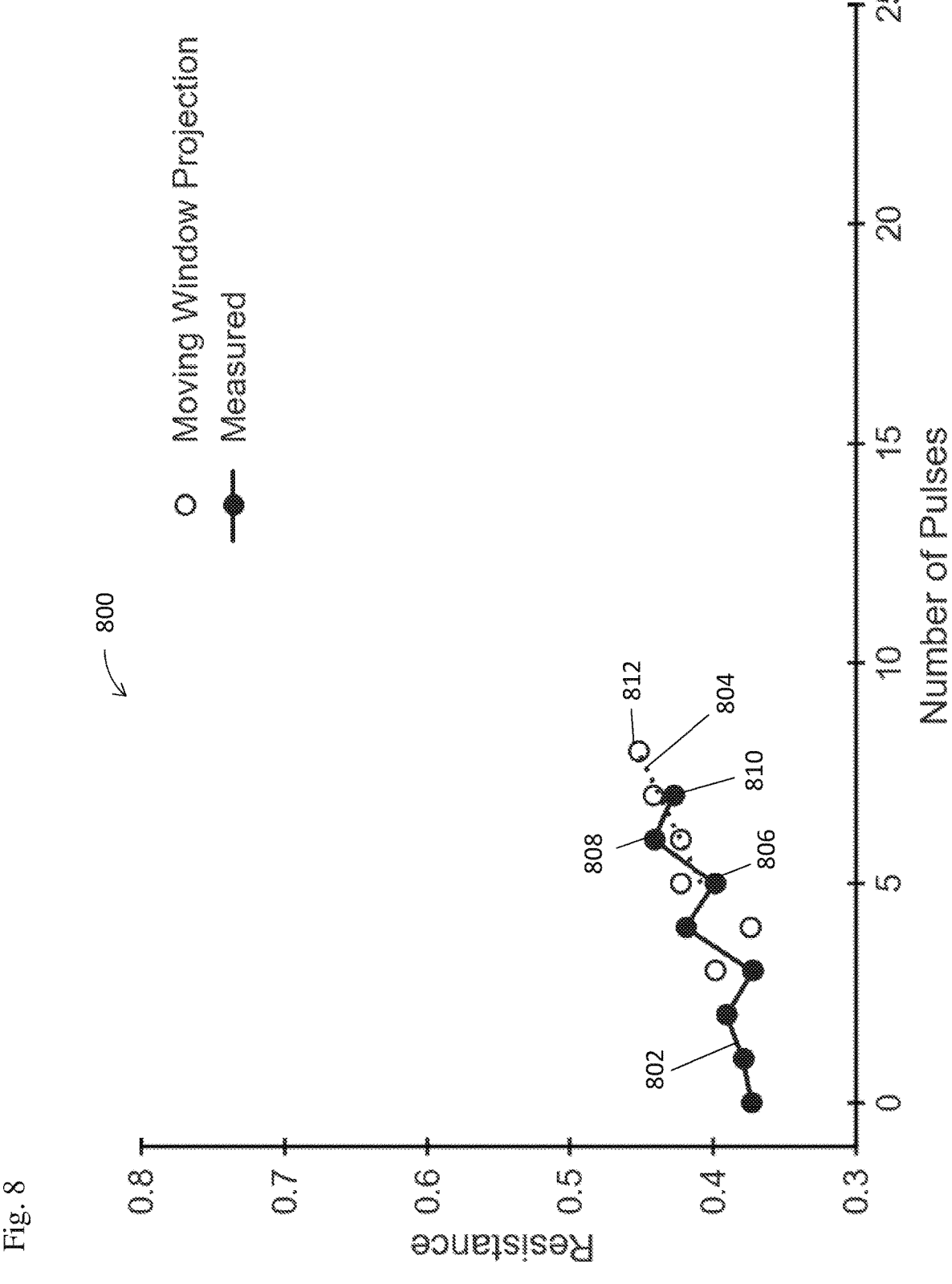
FIGS. 8-9 are graphs showing a predictive compensation technique employing a 'moving window' linear projection according to another example embodiment.

FIG. 8 illustrates a graph 800 including measured values of the chip resistance Rchip (line 802), and a linear projection (line 804) applied based on a 'moving window' linear projection. In this example, the chip resistance Rchip is assumed to increase linearly for local intervals (e.g., a piecewise linear increase). In the 'moving window projection method, the control circuit 108 of FIG. 1 determines a peak current value after detecting a decreasing current at two consecutive pulses. At the peak current, the value of the chip resistance Rchip is determined (e.g., measured, etc.). This resistance value on the line 802 is identified as point 806. At the peak current, the pulse point value P is set to equal 0. The value of the chip resistance Rchip is determined one or more times after the initial resistance value (e.g., after at P=0). In the particular example of FIG. 8, the control circuit 108 determines the value of the chip resistance Rchip at point 808 of the line 802 (corresponding to a pulse point value P=n−1), and the value of the chip resistance Rchip at point 810 of the line 802 (corresponding to a pulse point value P=n). In other examples, the control circuit 108 may determine more or less values of the chip resistance.

Next, a linear projection (the line 804) may be applied (e.g., linearly fit) from the pulse point value P=n−m to the pulse point value P=n (the most recent pulse point), where m is the data length of the piecewise (e.g., a defined number of electrical pulses over a local interval). In the example of FIG. 8, m is equal to 3 (e.g., points 806, 808, 810), and the point 810 is the most recent pulse point. Thus, in this particular example, the linear projection is linearly fit between the point 806 (e.g., P=n−m) and the point 810 (e.g., P=n), as shown in FIG. 8. This linear projection may then be used to predict a future value of the resistance (R_n+1) at the next pulse (e.g., the pulse point value P=n+1). This is shown as point 812 on the linear projection line 804. After the resistance (R_n+1) is predicted, the power source 106 may be controlled to provide a new voltage Vsys, new based on the predicted resistance value and the defined value (e.g., the peak current value) of the current Ichip, as shown in equation (12) above.

Figure 9:
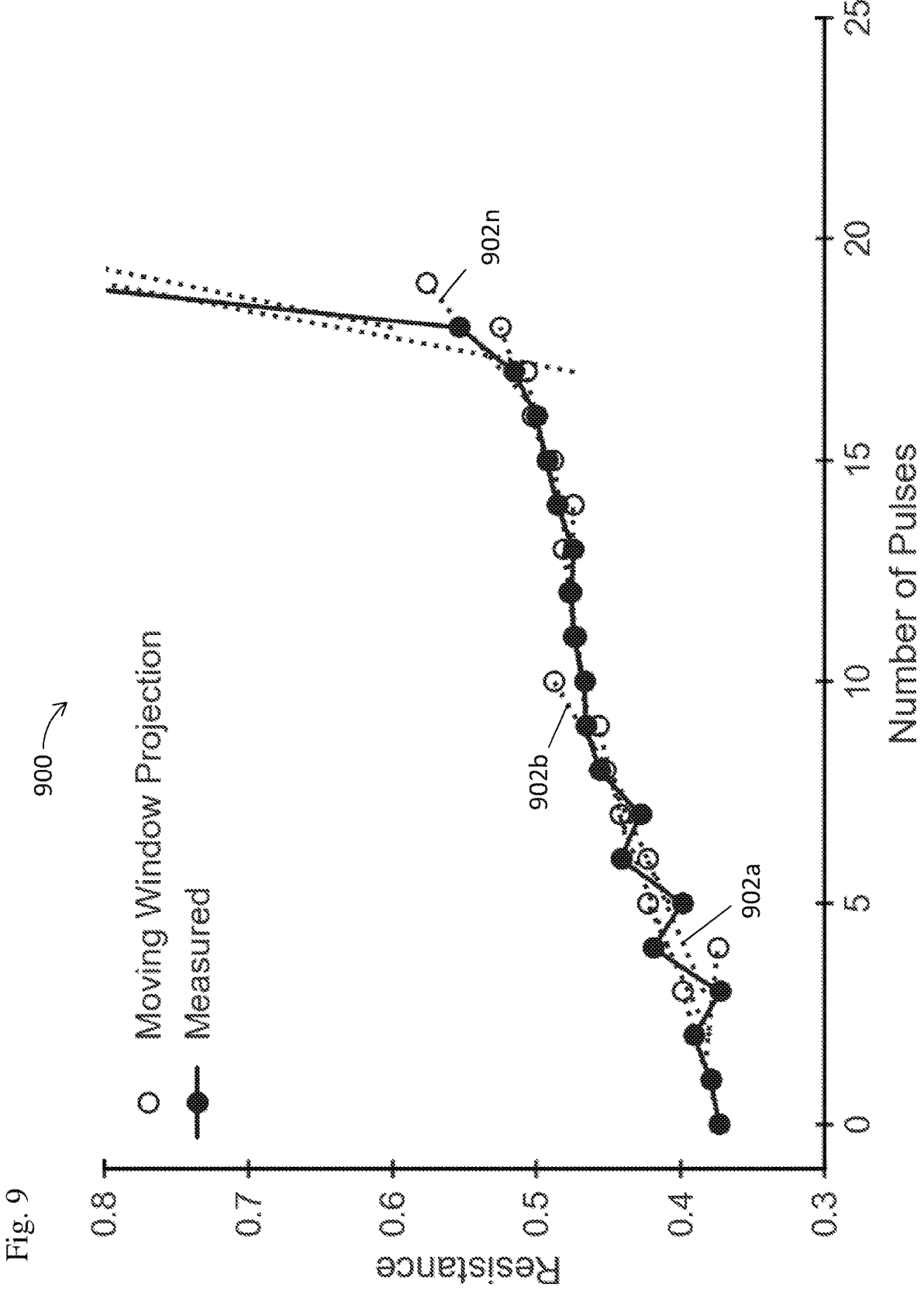

The 'moving window' linear projection process may be repeated as desired (e.g., to the end of the electroporation process) to predict the resistance at the next pulse and determine the voltage required to maintain the current Ichip at the defined value. For example, FIG. 9 illustrates a graph 900 showing multiple linear projections (e.g., lines 902*a-n*) being applied to predict resistances at future pulses. The data length of the piecewise (m) for each linear projection may be the same or different. By using the 'moving window' linear projection shown in FIGS. 8 and 9, the control circuit 108 may respond with an aggressive compensation approach for when the chip resistance Rchip changes non-linearly (e.g., a non-linear degradation). However, using the 'moving window' linear projection method may introduce undesired noise during the prediction process.

The control circuit 108 of FIG. 1 may employ various components and/or methods when employing the predictive compensation techniques explained above. For example, the 'all data' and 'moving window' linear projection techniques are based on linear regression for feedback control. In such examples, a simple gain factor G may be employed with the feedback control.

In other examples, the control circuit 108 may include a particular controller for feedback control. For example, the control circuit 108 may include may include a proportional-integral-derivative (PID) controller, a proportional-integral (P1) controller, a proportional-derivative (PD) controller, and/or a proportional (P) controller. Additionally, a gain factor of the PID controller, the P1 controller, the PD controller, and/or the P controller may be introduced to account for kinematics of the system. The feedback gain factor may be a fixed or variable value.

In some examples, the feedback gain factor may be machine learned from previous compensation results (based on on-line computations, an off-line database, etc.), etc. For example, the predictive compensation techniques may use machine learning methods based on known data points obtained in experiments, a historical database, etc. for the same cell lines being transfected or the same applications (e.g., protein production).

Figure 10:
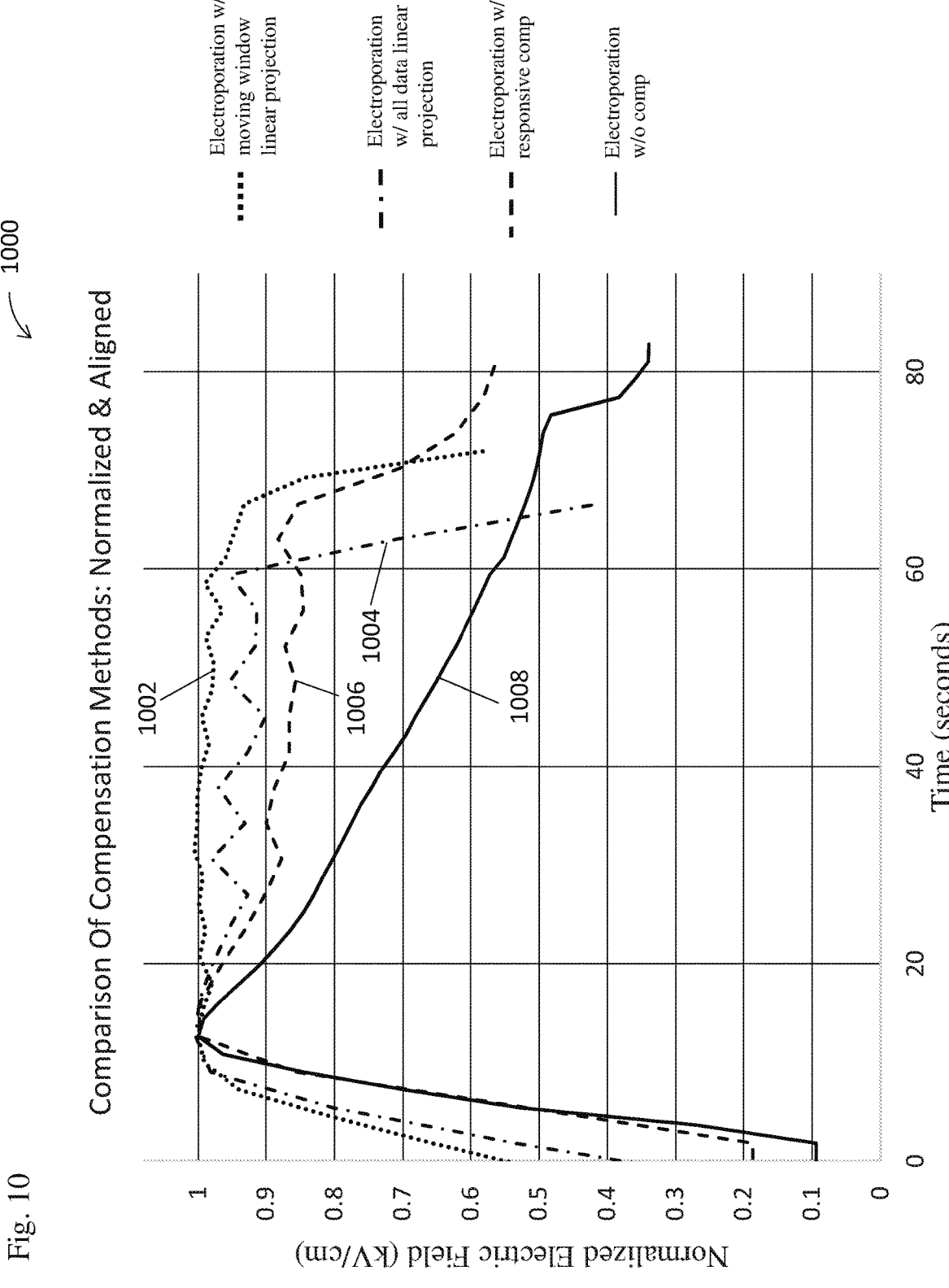
FIG. 10 is a graph showing electric field strengths when different predictive compensation techniques are employed according to another example embodiment.

Testing has shown that using 'moving window' linear projection may produce better compensation results during a degradation period than other compensation techniques. For example, FIG. 10 illustrates a graph 1000 including lines 1002, 1004, 1006, 1008 representing normalized electric field values over aligned period of time. Specifically, the line 1002 (having a dot-dot configuration) represents the electric field when a 'moving window' linear projection is applied, the line 1004 (having a dot-dash-dot configuration) represents the electric field when an 'all data' linear projection is applied, the line 1006 (having a dash-dash configuration) represents the electric field when a responsive compensation technique is applied, and the line 1008 (having a solid line configuration) represents the electric field when no compensation technique is applied. Degradation begins after the 10 second mark (e.g., when the normalized electric field values reach a peak), and compensation for the 'moving window' linear projection, the 'all data' linear projection, and the responsive techniques begins after detecting the degradation. As shown in FIG. 10, the electric field (the line 1002) corresponding to the 'moving window' linear projection technique is maintained at a normalized value of about one during the degradation period, the electric field (the line 1004) corresponding to the 'all data' linear projection technique is maintained at a normalized value of about 0.95 during the degradation period, and the electric field (the line 1006) corresponding to the responsive compensation technique is maintained at a normalized value of about 0.85 during the degradation period. As such, in the example of FIG. 10, the 'moving window' linear projection technique provides a better transfection efficiency than the 'all data' linear projection and responsive compensation techniques.

Figure 11:
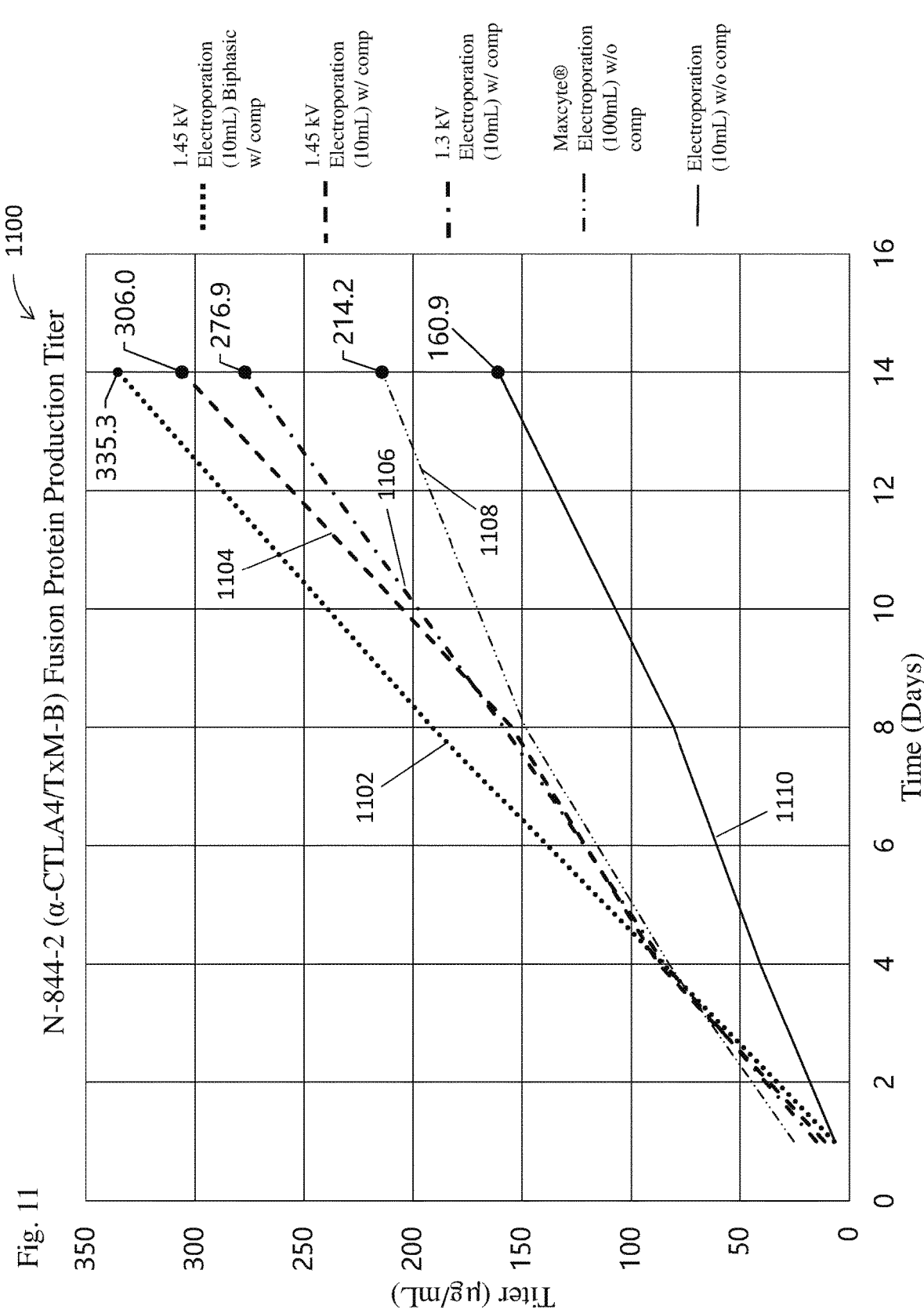
FIG. 11 is a graph showing biological performance outcomes when different compensation techniques are applied according to another example embodiment.

Additionally, electroporation processes using the 'moving window' linear projection technique may experience a greater yield than conventional electroporation processes. See Example 3 herein. For example, FIG. 11 illustrates a graph 1100 including lines 1102, 1104, 1106, 1108, 1110 representing biological performance outcomes when transfecting CHO-S cells with α-CTLA4/TxM-B fusion protein using different electroporation processes. In the example of FIG. 11, the CHO-S cells were transfected with an expression plasmid containing the DNA encoding the α-CTLA4/TxM-B fusion protein using the electroporation process with compensation applied by the 'moving window' linear projection technique as disclosed herein, or a conventional electroporation processes with no compensation. Specifically, the lines 1102, 1104, 1106 are associated with electroporation processes employing the 'moving window' linear projection technique during compensation, the line 1108 is associated with Maxcyte® electroporation process without compensation, and the line 1100 is a conventional electroporation process without compensation.

As shown, the titer line 1102 (having a dot-dot configuration) reaches 335.3 µg/mL when an electric field of 1.45 kV/cm is applied to a 10 mL biphasic sample, the titer line 1104 (having a dash-dash line configuration) reaches 306 µg/mL when an electric field of 1.45 kV/cm is applied to a 10 mL sample, and the titer line 1106 (having a dash-dot-dash line configuration) reaches 276.9 µg/mL when an electric field of 1.3 kV/cm is applied to a 10 mL sample. Additionally, the titer line 1108 (having a dash-dot-dot-dash line configuration) reaches 214.2 µg/mL for a 100 mL sample, and the titer line 1110 (having a solid line configuration) reaches 160.9 µg/mL for a 10 mL sample. As such, the transfection efficiency may be substantially higher when compensation is applied based on the 'moving window' linear projection technique (e.g., lines 1102, 1104, 1106) as compared to when no compensation is applied (e.g., lines 1108, 1110).

Figure 12:
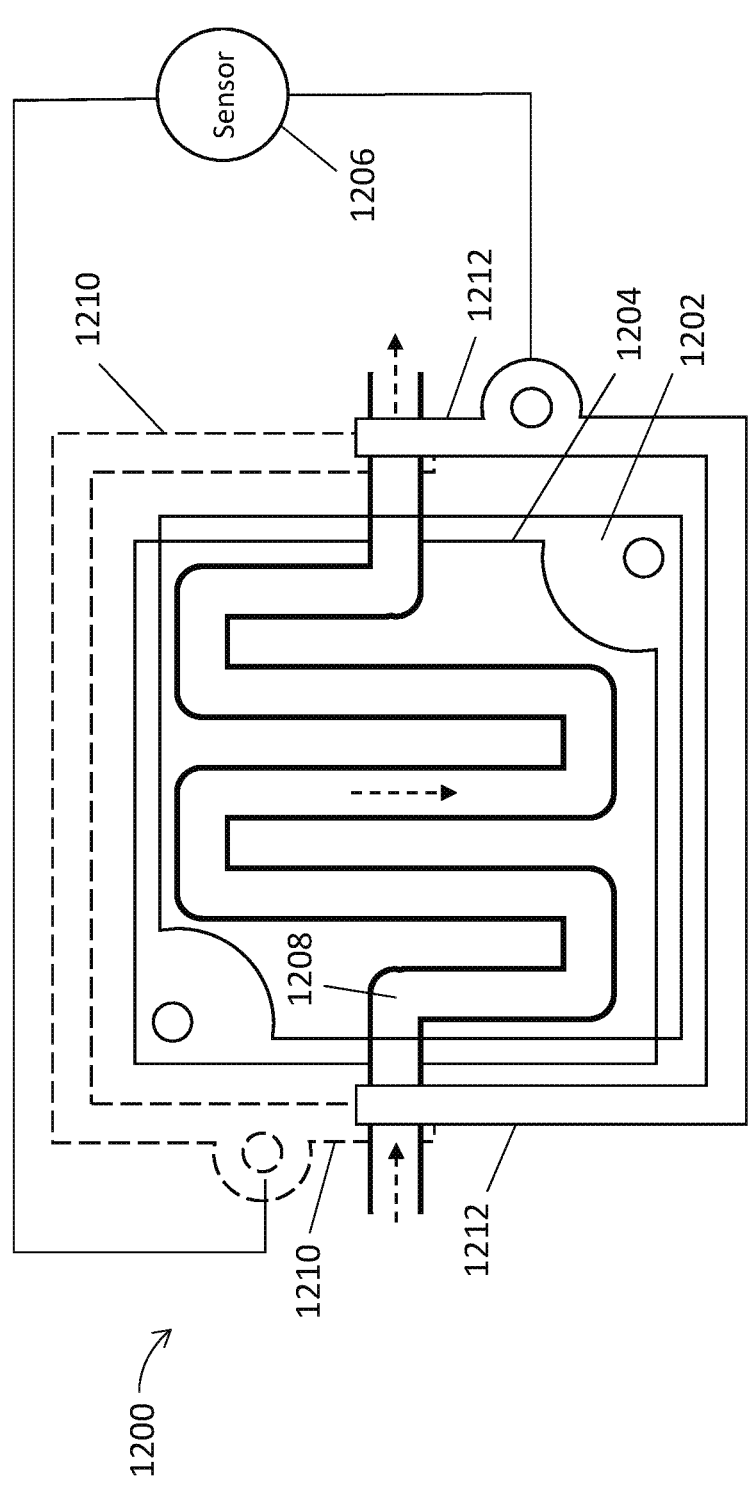
FIG. 12 is a block diagram of an electroporation apparatus including electrodes and sensor(s) for detecting when fluid is present between the electrodes according to another example embodiment.

In some examples, the control circuit (e.g., the control circuit 108 of FIG. 1) may monitor fluid flowing between electrodes, and control its associated DC power source to generate and/or stop generating electrical pulses in response to detecting one or more parameters associated with the fluid. For example, FIG. 12 illustrates an apparatus 1200 for electroporating cells with a cargo, and includes electrodes 1202, 1204, 1210, 1212, and a sensor 1206 coupled to the electrodes 1210, 1212. The electrodes 1202, 1204 are substantially similar to the electrodes 102, 104 of FIG. 1. As such, the electrodes 1202, 1204 may be spaced apart from each other and define a path 1208 for a fluid including the cells and the cargo to flow therebetween, as shown by dashed arrows. The path 1208 may have a serpentine configuration or any other suitable configuration.

As shown in FIG. 12, the electrodes 1210, 1212 are positioned on opposing sides of the electrodes 1202, 1204 at an inlet and an outlet of the path 1208 (e.g., a fluid channel). For example, and as shown in FIG. 12, the electrode 1210 (shown with a dashed line) is positioned on a bottom side of the electrodes 1202, 1204 at the inlet and the outlet, and the electrode 1212 (shown with a solid line) is positioned on a top side of the electrodes 1202, 1204 at the inlet and the outlet. The electrodes 1210, 1212 may be employed to detect fluid entering and exiting the fluid path 1208 between the electrodes 1202, 1204.

In the example of FIG. 12, the sensor 1206 may be in communication with or part of a control circuit (not shown) for controlling a DC power source (not shown) to compensate for electric field degradation as explained herein. The sensor 1206 may be a current sensor or an impedance sensor.

In the particular example of FIG. 12, fluid passing through the path 1208 is detected by sensing a current flowing through the electrodes 1210, 1212 and/or a resistance across the electrodes 1210, 1212 when a voltage is applied to the electrodes 1210, 1212. For example, fluid flowing through the path 1208 between the electrodes 1202, 1204 may cause a change in current passing through the electrodes 1210, 1212, and/or a change in the resistance across the electrodes 1210, 1212. In such examples, the sensor 1206 may detect this current and/or resistance change and send a signal to the control circuit indicating the electroporation process has begun (e.g., fluid is flowing between the electrodes 1210, 1212), is ending, etc.

Figure 13:
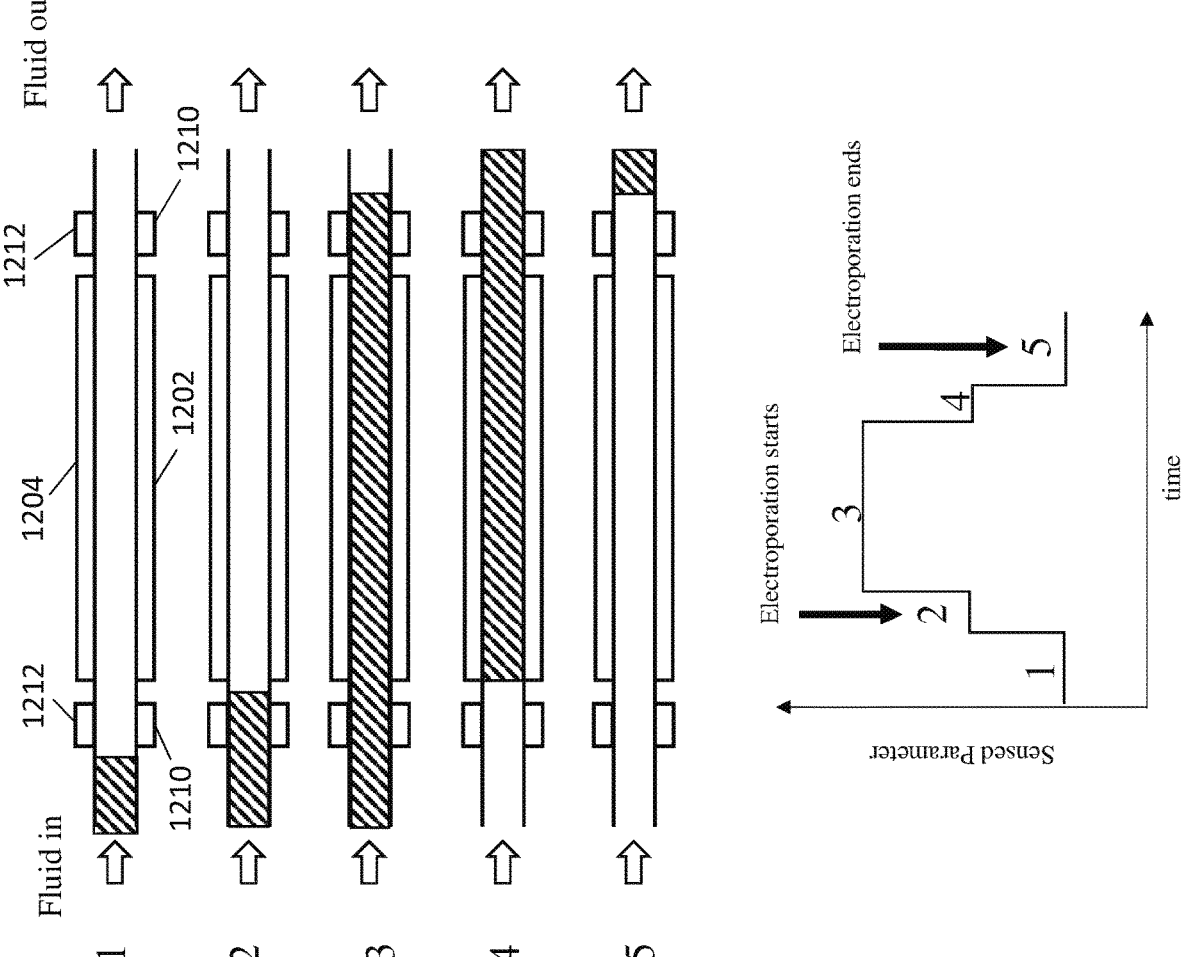
FIG. 13 is a block diagram of fluid flow in the electroporation apparatus of FIG. 12.

For example, FIG. 13 illustrates fluid flow for five stages and a graph of the sensed parameter (e.g., the current or resistance) associated with the electrodes 1210, 1212 over the five stages. In the first stage, fluid has not reached the electrodes 1210, 1212, and the sensed parameter remains at an initial state (e.g., a steady state value with no fluid). In the second stage, fluid passes the electrodes 1210, 1212 at the inlet of the path 1208 causing the sensed parameter to increase. In the third stage, fluid passes the electrodes 1210, 1212 at the inlet and the outlet of the path 1208 causing the sensed parameter to increase again. In the fourth stage, fluid passes the electrodes 1210, 1212 at the outlet of the path 1208 causing the sensed parameter to decrease. In the fifth stage, fluid has passed the electrodes 1210, 1212 causing the sensed parameter to decrease again (e.g., back to its steady state value). As such, the control circuit may control the DC power source to generate electrical pulses based on the increased parameter (e.g., when fluid is present in stages 2-4), and to stop generating the electrical pulses based on the steady state parameter (e.g., in stage 5). Additionally, if it is known when the electric field begins to degrade in relation to when fluid is present, the control circuit may begin controlling the DC power source to compensate for electric field degradation when the chamber is filled with fluid (e.g., stage 3). This may allow the control circuit to begin its compensation process at an earlier point in time as compared to other techniques based on, for example, detecting a decrease in current provided by the DC power source.

Figures 14, 15:
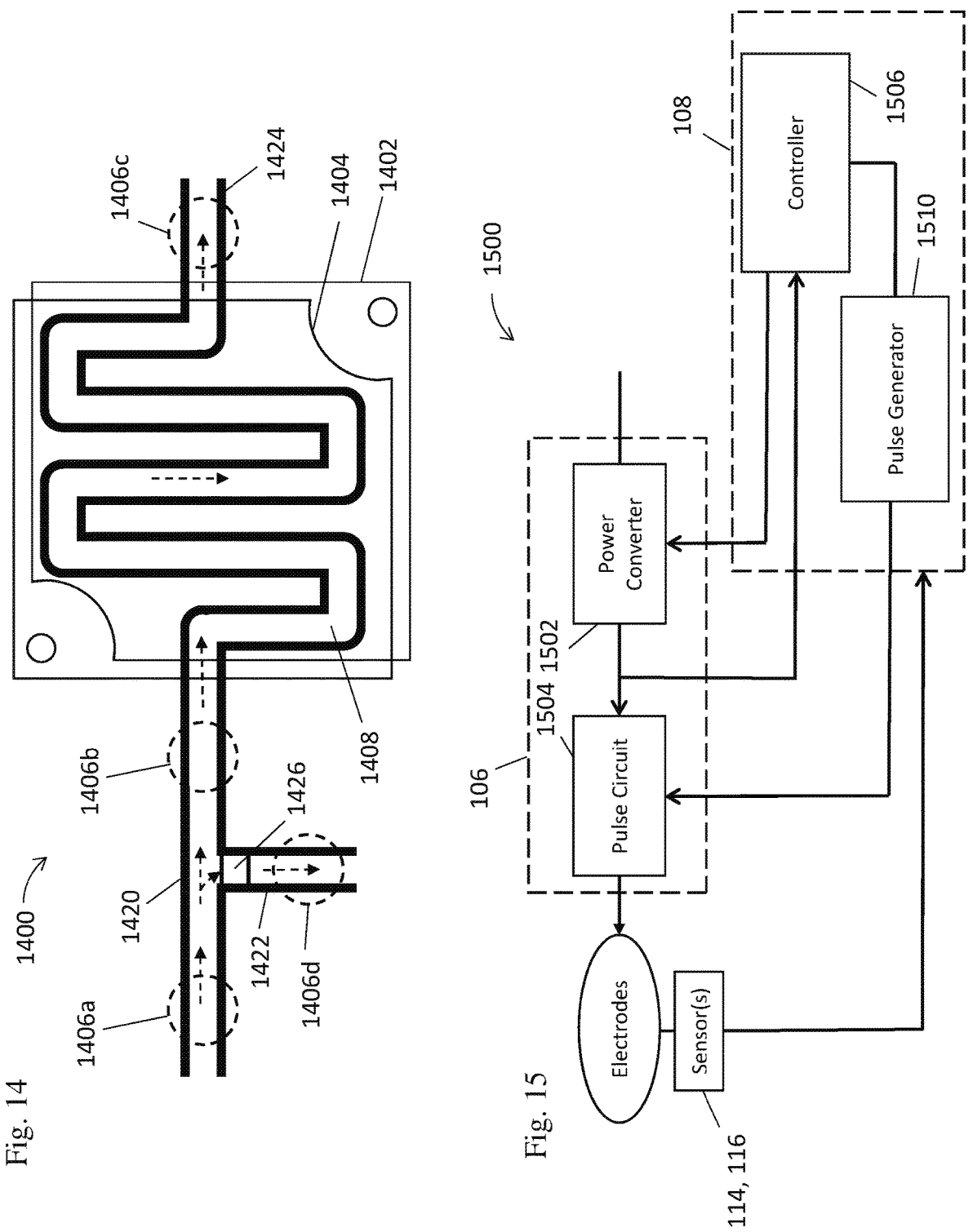
FIG. 14 is a block diagram of electrodes employable in the electroporation apparatus of FIG. 1, according to another example embodiment.
FIG. 15 is a block diagram of a power source and a control circuit employable in the electroporation apparatus of FIG. 1, according to another example embodiment.

FIG. 14 illustrates another apparatus 1400 that may monitor fluid flowing between electrodes, and control its associated DC power source to generate and/or stop generating electrical pulses in response to detecting one or more parameters associated with the fluid. For example, and as shown in FIG. 14, the apparatus 1400 includes fluid paths 1420, 1422, 1424, a check valve 1426 in the fluid path 1422, sensors 1406a-d in fluid communication with the paths 1420, 1422, 1424, and the electrodes 1202, 1204 of FIG. 12 defining the path 1208. As shown, the fluid path 1208 (between the electrodes 1202, 1204) is coupled between fluid paths 1420, 1424, and the fluid path 1422 (e.g., a lateral path) extends from the fluid path 1420. In the example of FIG. 13, the sensors 1406a-d may be in communication with or part of a control circuit (not shown) for controlling a DC power source (not shown) to compensate for electric field degradation as explained herein.

Once the electroporation process has begun, fluid begins to flow through the paths 1208, 1420, 1422, 1424, as shown by the dashed arrows. Specifically, fluid flows through the path 1420 (e.g., an inlet path), into the path 1208, and exits through the path 1424 (e.g., an outlet path). In such examples, one or both sensors 1406*a-b* may sense fluid flowing into the path 1208 (e.g., into the chip) and send a signal to the control circuit. This allows the control circuit to detect a presence of fluid indicating the electroporation process has begun. As such, the control circuit may control the DC power source to generate electrical pulses based on the presence of fluid. The control circuit may then begin controlling the DC power source to compensate for electric field degradation in response to any one of the sensors 1406*a-c* detecting the presence of fluid. This may begin the compensation process at an earlier point in time as compared to other techniques based on, for example, detecting a decrease in current provided by the DC power source.

Additionally, the control circuit may stop the electroporation process based on a parameter associated with the fluid. For example, the sensor 1406*c* may sense a decrease in fluid and/or an absence of fluid indicating the fluid has passed through the path 1208 (e.g., through the chip) and that the electroporation process has finished. In such examples, the sensor 1406*c* may send a signal to the control circuit, and the control circuit may control the DC power source to stop generating the electrical pulses (e.g., stopping the electroporation process) and/or control a fluid pump to turn off.

In some examples, the check valve 1426 may function as an occlusion detector to sense a blockage of the fluid in one of the paths 1208, 1420, 1424. For example, pressure may build up on in the inlet side of the check valve 1426 if a blockage of the fluid is present. If the pressure exceeds a defined trip threshold (e.g., 20-40 psi) of the check valve 1426, the check valve 1426 may open allowing fluid to flow through the path 1422 and past the sensor 1406*d* positioned on the outlet side of the valve 1426. In such examples, the sensor 1406*d* detects the fluid (indicating a blockage in one of the paths 1208, 1420, 1424) and sends a signal to the control circuit to stop generating the electrical pulses and/or stop the fluid pump. In other examples, the check valve 1426 may send a signal to the control circuit based on a state of the valve 1426 (e.g., open or closed) to indicate whether a blockage exists. In such examples, the sensor 1406*d* may not be employed.

The sensors 1406*a-d* may be any suitable sensors. For example, any one of the sensors 1406*a-d* may be an ultrasonic sensor, a light sensor (e.g., an infrared sensor), etc. In such examples, fluid may be detected by waves and/or light reflecting of the fluid, traveling through the fluid, etc. The light sensors may provide and/or detect visible or nonvisible light. In some examples, one or more light sources such as LEDs, lasers, infrared lights, etc. may be employed in conjunction with the sensors 1406*a-d* and/or be a part of the sensors 1406*a-d*. Additionally, in the particular example of FIG. 13, the four sensors 1406*a-d* are positioned outside the electrodes 1202, 1204. In other examples, any one of the sensors 1406*a-d* may be positioned along the path 1208 (e.g., between the electrodes 1202, 1204) if desired. Further, in some examples, only one sensor (e.g., the sensor 1406*a*, the sensor 1406*b*, etc.) may be utilized, more than four sensors may be utilized, etc.

The electrodes disclosed herein may be any suitable type of electrically conductive electrodes. For example, any one of the electrodes 102, 104, 1202, 1204, 1210, 1212 may include a meshed plate having a porosity to allow the passage of fluid including the cells and the cargo, a solid plate, etc.

Additionally, the power sources and the control circuits disclosed herein may include various suitable components. For example, FIG. 15 illustrates an apparatus 1500 including the DC power source 106 and the control circuit 108 of FIG. 1. In the example of FIG. 15, the DC power source 106 includes a power converter 1502 and a pulse circuit 1504. The power converter 1502 may include DC-DC power conversion circuitry and/or AC-DC power conversion circuitry having any suitable converter topology. For example, the power converter 1502 may receive DC or AC power, and output a regulated DC voltage to the pulse circuit 1504. In some examples, the power source 106 may include an AC-DC rectifier and DC-DC buck, boost, etc. conversion circuitry coupled to the AC-DC rectifier.

The pulse circuit 1504 of FIG. 15 receives the regulated DC voltage from the power converter 1502, and converts the DC voltage into DC electrical pulses. The electrical pulses are then provided to electrodes (e.g., the electrodes 102, 104 of FIG. 1, the electrodes 1202, 1204 of FIG. 12, etc.), as explained herein. For example, the pulse circuit 1504 may include one or more switching devices for interpreting the DC voltage from the power converter 1502 and creating the electrical pulses.

In the example of FIG. 15, the control circuit 108 includes a controller 1506 and a pulse generator 1508 coupled to the controller 1506. As shown, the controller 1506 receives a feedback signal representing an output parameter (e.g. the output voltage) of the power converter 1502, and provides one or more control signals to the power converter 1502 for controlling one or more switching devices in the power converter 1502 based on the feedback signal. In some examples, the controller 1506 may control the power converter's switching devices to regulate the output voltage of the power converter at different set values based on a voltage Vchip sensed by the voltage sensor 116 of FIG. 1 and/or an induced current Ichip sensed by the current sensor 114 of FIG. 1. As such, the controller 1506 may control the amplitude of the electrical pulses. In such examples, the controller 1506 may control the output of the power converter 1502 to compensate for electric field degradation, as explained herein.

The controller 1506 provides a signal to the pulse generator 1508, and the pulse generator 1508 provides one or more control signals to the pulse circuit 1504 for controlling its switch device(s) to generate the electrical pulses based on the received signal from the controller 1506. In some examples, the pulse generator 1508 may adjust the frequency, pulse width, duty cycle, etc. of the electrical pulses based on the received signal from the controller 1506.

EXAMPLES

Example 1 (FIGS. 2 and 3)

Cell preparation: Gibco™ CHO-S™ cells (ThermoFisher Cat. A11557-01) were expanded in CD-CHO medium (ThermoFisher Cat. 10743029)+8 mM L-glutamine before the experiment. The CHO-S cells were cultured and harvested at a concentration of <2e6 cells/mL. At Day 0 of the experiment, a 5% home-made sodium based electroporation buffer at 37° C. existed, and at Day 1 of the experiment, 1 mM of sodium butyrate was added and the 5% home-made sodium based electroporation buffer was moved to 32° C. The home-made sodium based electroporation buffer was fed at Day 4 and Day 8 of the experiment. The viability and VCD (viable cell density) follow similar trend lines during the electroporation processes.

Cells were harvested and washed with the home-made sodium based electroporation buffer (sodium concentration 8 mM/L, conductivity=10-14 mS/cm, osmolarity=265-300 mOSM/L, pH 7.2-7.4) and resuspended in the same home-made sodium based buffer with cell density of 100e6 cells/mL. An example of the home-made sodium based electroporation buffer is shown below in Table 2:

TABLE 2

| Solute | | brand/Cat# used | MW | Molar concentration (mol/L) |
|---|---|---|---|---|
| KCL | Potassium chloride | Fluka, 60129 | 74.55 | 0.1 |
| Na₂HPO₄ | Sodium phosphate dibasic | Sigma, S3397 | 141.96 | 0.008 |
| MgCL2 | Magnesium chloride | Sigma, M8266 | 95.211 | 0.001 |
| D-(+)-Glucose | Glucose | Sigma, G7021 | 180.156 | 0.04 |
| HEPES | HEPES | Fisher BP310 | 238.3 | 0.025 |

Conductivity = 12 mS/cm
Osmolarity = ~278 mOsm/L

α-CTLA-4/TxM-B fusion protein (N-844-2) DNA preparation: N-844-2 is an anti-CTLA-4/TxM molecule, in which anti-CTLA-4 scFv is attached to the IL-15RαSu moiety. Preparation and disclosure of anti-CTLA-4 scFv/IL-15RαSu molecule is disclosed in WO 2018/075989, which is incorporated herein by reference in its entirety. The DNA sequence of N-844-2 was cloned into a mammalian expression plasmid. The DNA plasmid containing the N-844-2 sequence was then prepared in milligram quantity using Endo Free DNA Giga kit (Qiagen Cat. No. 12391). The expression plasmid containing the DNA encoding the α-CTLA4/TxM-B fusion protein was diluted in water and mixed with the cell suspension right before the electroporation process.

Electroporation: Mixed cells and DNA suspension were placed in a 50 mL falcon tube and pumped into the electroporation chip with a peristaltic pump and tubings. The pulse waveform was 40V, pulse width was 450 µs, pulse interval was 2.7 seconds, flow rate was 2 ml/min. The voltage V(p) and current I(p) were recorded for the entire experiment as a function of each pulse (p), and the resistance R(p) was calculated as R(p)=V(p)/I(op). R0=min(R(p)) was when the fluid fully filled the electroporation chamber, which is set as the initial electrode-fluid interface resistance Ri in FIG. 1. The effective electrical field was calculated as E=V(p)*R0/(R(p)*d), d was the distance between electrode pairs. FIG. 2 and FIG. 3: V, I, R, E were then plotted as a function number of pulse p.

Example 2 (FIG. 4)

Cell preparation and α-CTLA-4/TxM-B fusion protein (N-844-2) DNA preparation was the same as Example 1.

Electroporation: Mixed cells and DNA suspension were placed in 1.5 mL tubes and pumped into the electroporation chip with peristaltic pump and tubings. Four different total volumes of the cell and DNA mixture were tested in this experiment: 120 µL, 240 µL, 400 µL and 600 µL. The pulse waveform was 38V, pulse width was 450 µs, pulse interval was 0.27 seconds, and flow rate was 1 mL/min. The voltage V(p) and current I(p) were recorded for the entire experiment as a function of each pulse (p), and the resistance R(p) was calculated as R(p)=V(p)/I(op). R0=min(R(p)) was when the fluid fully filled the electroporation chamber, which was set as the initial electrode-fluid interface resistance Ri in FIG. 1. The effective electrical field was calculated as E=V(p)*R0/(R(p)*d), d was the distance between electrode pairs. FIG. 4: effective electrical field E was then plotted as a function number of pulse p.

Example 3 (FIG. 11)

Cell preparation and α-CTLA-4/TxM-B fusion protein (N-844-2) DNA preparation was the same as Example 1.

Electroporation: Mixed cells and DNA suspension were placed in 50 mL tubes and pumped into the electroporation chip with peristaltic pump and tubings. Five different electroporation conditions were compared with same cell preparation as described above. The five different conditions are shown in Table 3 below:

TABLE 3

| Experiment | Condition |
|---|---|
| 1.45 kV Electroporation (10 mL) Biphasic w/compensation | The pulse waveform was 45 V, pulse width was 600 µs, pulse interval was 6.75 seconds, flow rate was 1.2 mL/min. Biphasic pulse train. |
| 1.45 kV Electroporation (10 mL) w/compensation | The pulse waveform was 46 V, pulse width was 500 µs, pulse interval was 5.4 seconds, flow rate was 1.5 mL/min. Monophasic pulse train. |
| 1.3 kV Electroporation (10 mL) w/compensation | The pulse waveform was 37 V, pulse width was 450 µs, pulse interval was 3.6 seconds, flow rate was 1.5 mL/min. Monophasic pulse train. |
| Maxcyte ® Electroporation (100 mL) | Use Maxcyte ® CHO cell program (parameters unknown) |
| Electroporation (10 mL) w/o compensation | The pulse waveform was 40 V, pulse width was 450 µs, pulse interval was 2.7 seconds, flow rate was 1.0 mL/min. Monophasic pulse train. |

FIG. 11 shows that with the compensation method, there is an improved protein production titer outcome. Titer was measured using Protein A biosensor on Octet Red 96e with the standard curve prepared using N-601 (a monoclonal IgG1 antibody).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An apparatus for electroporating cells with a cargo, the apparatus comprising:

two electrodes spaced apart from each other and defining a path for a fluid including the cells and the cargo to flow therebetween;

a DC power source coupled across the electrodes for providing a plurality of electrical pulses to induce a current through the electrodes for generating an electric field between the electrodes; and a control circuit configured to detect a presence of fluid, and in response to detecting the presence of fluid control the DC power source to generate the plurality of electrical pulses, detect an absence of fluid, and in response to detecting the absence of fluid, control the DC power source to stop generating the plurality of electrical pulses, and wherein the control circuit is further configured to detect a decrease in the induced current due to an increase in a resistance between the electrodes, and provide predictive compensation by increasing the induced current based on feedback of at least one of a proportional-integral-derivative (PID) controller, a proportional-integral (PI) controller, a proportional-derivative (PD) controller, and a proportional (P) controller in order to maintain the electric field between the electrodes at a defined value.

2. The apparatus of claim 1, further comprising a first sensor and a second sensor coupled to the control circuit, the first sensor in fluid communication with the path for detecting the presence of fluid, and the second sensor in fluid communication with the path for detecting the absence of fluid.

3. The apparatus of claim 2, wherein at least one of the first sensor and the second sensor includes a light sensor.

4. The apparatus of claim 1, further comprising a feedback gain factor of the PID controller, the PI controller, the PD controller, and/or the P controller, wherein the feedback gain factor is a fixed value or a variable value.

5. The apparatus of claim 4, wherein the feedback gain factor is machine learned from previous compensation results.

* * * * *